US011179060B2

(12) United States Patent (10) Patent No.: US 11,179,060 B2
Odame et al. (45) Date of Patent: Nov. 23, 2021

(54) WEARABLE SYSTEM FOR AUTONOMOUS DETECTION OF ASTHMA SYMPTOMS AND INHALER USE, AND FOR ASTHMA MANAGEMENT

(71) Applicant: THE TRUSTEES OF DARTMOUTH COLLEGE, Hanover, NH (US)

(72) Inventors: Kofi Odame, Hanover, NH (US); Justice Amoh, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 548 days.

(21) Appl. No.: 15/742,510

(22) PCT Filed: Jul. 7, 2016

(86) PCT No.: PCT/US2016/041308
§ 371 (c)(1),
(2) Date: Jan. 7, 2018

(87) PCT Pub. No.: WO2017/007919
PCT Pub. Date: Jan. 12, 2017

(65) Prior Publication Data
US 2018/0199855 A1 Jul. 19, 2018

Related U.S. Application Data

(60) Provisional application No. 62/189,435, filed on Jul. 7, 2015.

(51) Int. Cl.
*A61B 5/08* (2006.01)
*G06F 16/22* (2019.01)
(Continued)

(52) U.S. Cl.
CPC .......... *A61B 5/0823* (2013.01); *A61B 5/6822* (2013.01); *A61B 5/6823* (2013.01);
(Continued)

(58) Field of Classification Search
None
See application file for complete search history.

(56) References Cited

U.S. PATENT DOCUMENTS 5,853,005 A * 12/1998 Scanlon ................. A61B 5/113
600/459
6,139,505 A * 10/2000 Murphy ................. A61B 5/061
381/67

(Continued)

FOREIGN PATENT DOCUMENTS

WO WO 2011/123071 A1 10/2011
WO WO-2014033229 A1 * 3/2014 ........ A61M 15/0065

OTHER PUBLICATIONS

Emanet, N., Öz, H., Bayram, N. and Delen, D., 2014. A comparative analysis of machine learning methods for classification type decision problems in healthcare. Decision Analytics, 1(1). (Year: 2014).*
PCT/US2016/041308 International Search Report and Written Opinion dated Sep. 27, 2016, 14 pp.

*Primary Examiner* — Jason M Sims
*Assistant Examiner* — James Stewart Stambaugh, III

(57) ABSTRACT

A system adapted to assisting patients manage asthma includes a wearable sensor for detection of asthma symptoms and inhaler use, having a microphone capable of generating an electrical signal indicative of asthma symptoms or inhaler use; a processor with firmware adapted to process the electrical signal to determine potential asthma symptoms and inhaler use; and store the electrical signal in the memory when the electrical signal potentially corresponds asthma symptoms or inhaler use. In particular embodiments, the system includes an electronic asthma diary including detected asthma symptoms and detected inhaler usage, both with timestamps, and a prescribed treatment protocol. Protocol firmware processes detected asthma symptoms an inhaler usage recorded in the asthma diary to determine if asthma is controlled, and if asthma is not
(Continued)

determined controlled determines if a treatment change is authorized; if treatment change is authorized the treatment change is displayed in human-readable form.

15 Claims, 8 Drawing Sheets

(51) Int. Cl.
  *A61B 5/00* (2006.01)
  *G16H 20/10* (2018.01)
  *G16H 40/67* (2018.01)
  *G16H 10/60* (2018.01)
  *A61B 7/00* (2006.01)
  *A61B 5/087* (2006.01)

(52) U.S. Cl.
  CPC ............ *A61B 5/725* (2013.01); *A61B 5/7207* (2013.01); *A61B 7/003* (2013.01); *G06F 16/22* (2019.01); *G16H 10/60* (2018.01); *G16H 20/10* (2018.01); *G16H 40/67* (2018.01); *A61B 5/0024* (2013.01); *A61B 5/087* (2013.01); *A61B 5/486* (2013.01); *A61B 5/7267* (2013.01); *A61B 2562/0204* (2013.01); *A61B 2562/0219* (2013.01); *A61B 2562/0247* (2013.01); *A61B 2562/0261* (2013.01)

(56) References Cited

U.S. PATENT DOCUMENTS

| | | | |
|---|---|---|---|
| 6,587,564 B1* | 7/2003 | Cusson | A61B 7/04 181/131 |
| 6,662,032 B1* | 12/2003 | Gavish | A61B 5/486 600/323 |
| 7,037,268 B1 | 5/2006 | Sleva et al. | |
| 7,850,619 B2 | 12/2010 | Gavish et al. | |
| 8,807,131 B1 | 8/2014 | Tunnell et al. | |
| 2006/0241510 A1* | 10/2006 | Halperin | A61B 5/7275 600/534 |
| 2008/0114266 A1* | 5/2008 | Shen | A61B 7/003 600/586 |
| 2009/0018409 A1 | 1/2009 | Banet et al. | |
| 2009/0314292 A1* | 12/2009 | Overfield | A61M 15/0021 128/203.15 |
| 2010/0204550 A1 | 8/2010 | Heneghan et al. | |
| 2011/0125044 A1* | 5/2011 | Rhee | A61B 5/113 600/534 |
| 2012/0172676 A1* | 7/2012 | Penders | A61B 7/008 600/301 |
| 2012/0265024 A1* | 10/2012 | Shrivastav | G16H 50/30 600/300 |
| 2012/0265545 A1* | 10/2012 | Hwang | G06Q 10/10 705/1.1 |
| 2014/0122122 A1 | 5/2014 | Cooper et al. | |
| 2014/0257126 A1* | 9/2014 | Vink | A61B 5/08 600/529 |

* cited by examiner

WEARABLE SYSTEM FOR AUTONOMOUS DETECTION OF ASTHMA SYMPTOMS AND INHALER USE, AND FOR ASTHMA MANAGEMENT

CROSS-REFERENCE TO RELATED APPLICATIONS

This application is a 35 U.S.C. § 371 filing of International Application No. PCT/US2016/041308, filed 7 Jul. 2016, which claims the benefit of priority to U.S. Provisional Patent Application No. 62/189,435 filed 7 Jul. 2015, the contents of which are incorporated herein by reference in its entirety.

U.S. GOVERNMENT RIGHTS

This invention was made with Government support under grant No. ECCS-1128478 awarded by National Science Foundation. The Government has certain rights in this invention.

BACKGROUND

Asthma episodes account for 1.8 million emergency department visits in the United States each year. These emergency department visits cost the health care system approximately $23 billion each year. Self-management regimes, including monitoring symptoms and medication use, have proven to reduce these visits by as much as 40%. Asthma episodes can also be quite uncomfortable for patients and their families, and at times life-threatening.

Current methods for tracking asthma medication use rely on either attaching sensors to inhalers, or manually recording frequency of use.

Current methods for managing asthma often rely on a manually-recorded asthma diary, with frequent visits to a physician for adjustment of medication.

Asthma patients are often prescribed one or more medications of one or more classes. One class of medications often prescribed is a short acting beta agonist, such as Albuterol (salbutamol), or a longer-acting beta agonist; these are generally administered by inhalation using an inhaler or a nebulizer, cause dilation of airway passages, and typically give short term relief from symptoms. Other medications often prescribed include longer-acting "controller" medications, of which patients are often prescribed one or more classes. Classes of controller medications include oral steroids such as Prednisone, immune modulators such as montelukast, and inhaled steroids such as fluticasone or budesonide, as well as longer-acting beta agonists administered through an inhaler or nebulizer. Some patients are prescribed combination medications, such as Advair or Symbicort, including both an inhaled steroid and an inhaled long-acting beta agonist. Since some patients have episodes triggered by allergies, some patients are also prescribed antihistamines as part of their asthma management.

Asthma episodes can be triggered by a range of triggering events, ranging from cold weather through viral infections and exercise to allergies both seasonal and to foods. Patients differ widely in triggers, severity and extent of resulting episodes, and responses to medications. Sometimes these events can be identified and minimized and responded to with appropriate treatment ranging from medications through allergy desensitization injections and influenza vaccines.

Medications have side effects. Oral steroids can lead to central obesity as a result of fat redistribution, as well as excessive blood glucose levels, or growth disturbance. Inhaled steroids can predispose to, or mask, certain infections. Beta agonists raise blood pressure as well as heart rate. Most physicians seek to limit these side effects by administering medications in amounts needed by a patient when the patient needs them; and phasing out or administering smaller doses less frequently when patients are in less need of medications.

Traditional asthma management relies on verbal reports of frequency and severity of episodes from patients and parents, and often involves increases of potency and frequency of controller medication usage when symptoms or triggers are frequent, and decreases when symptoms are rare.

SUMMARY

A system adapted to assisting patients manage asthma includes a wearable sensor for detection of asthma symptoms and inhaler use, having a microphone capable of generating an electrical signal indicative of asthma symptoms or inhaler use; a processor with firmware adapted to process the electrical signal to determine potential asthma symptoms and inhaler use; and store the electrical signal in the memory when the electrical signal potentially corresponds asthma symptoms or inhaler use. In particular embodiments, the system includes an electronic asthma diary including detected asthma symptoms and detected inhaler usage, both with timestamps, and a prescribed treatment protocol. Protocol firmware processes detected asthma symptoms and inhaler usage recorded in the asthma diary to determine if asthma is controlled, and if asthma is not determined controlled, determines if a treatment change is authorized; if treatment change is authorized the treatment change is displayed in human-readable form.

A method for autonomous detection of asthma symptoms and inhaler use includes: digitizing an electrical signal from a microphone; evaluating a portion of the digitized signal for relevance to detecting the asthma symptoms and for detecting inhaler use; and storing the portion of the digitized signal if it is determined relevant. Relevant signal portions are then transmitted to an external device for further processing.

DETAILED DESCRIPTION OF THE EMBODIMENTS

Most asthma is monitored through a manually-recorded asthma diary. Symptoms and treatments as recorded in the diary, including frequency of asthma attacks, frequency of less severe wheezing, patient impressions of possible triggering events, medication and inhaler use, are then brought to a physician who then issues new or changed prescriptions and advises the patient how to better manage their asthma.

Figure 1:
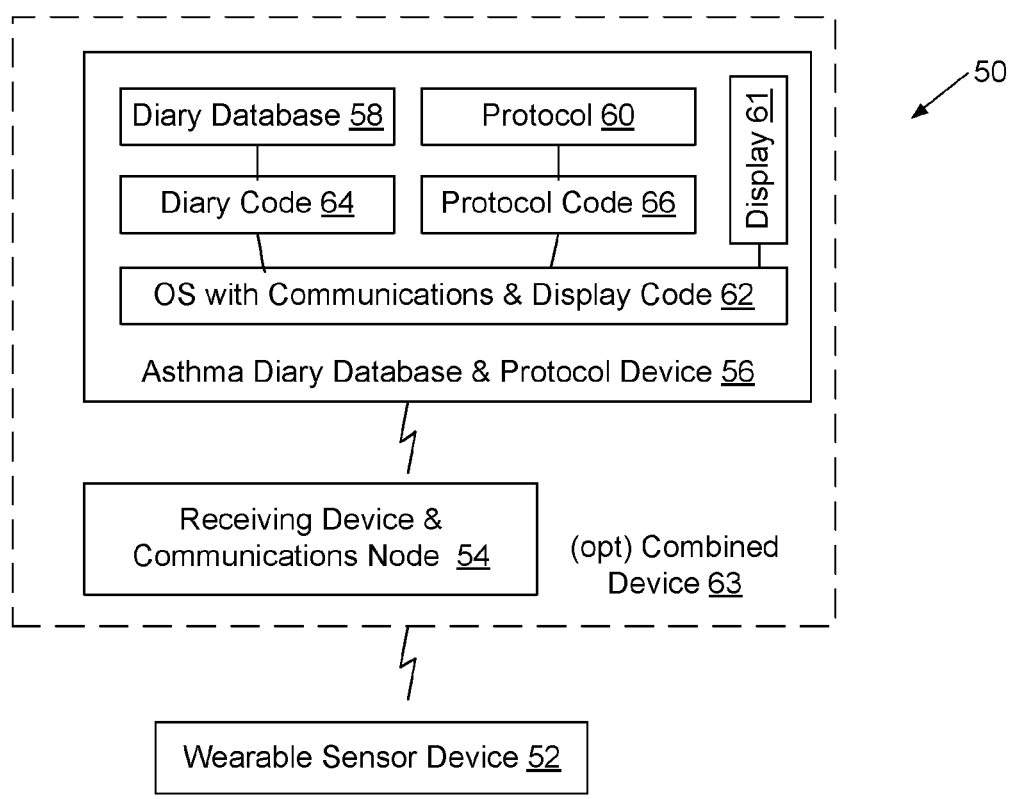
FIG. 1 illustrates a system for asthma management including a wearable sensor and using an automated asthma log and treatment protocol.

We desire to improve asthma management by automating and improving accuracy of data gathering over a manual diary, and by using an automated, physician-prescribed, asthma-management protocol to help patients better manage their asthma between physician visits. In an embodiment, in order to help patients manage asthma, we propose an asthma management system 50 (FIG. 1). The asthma management system 50 has three key components, a wearable sensor 52 (FIG. 1), 100 (FIG. 2), a receiving device 54 (FIG. 1), 150 (FIG. 2) that receives data wirelessly from receiving device 52, 100 and processes that data to detect asthma symptoms and inhaler usage, and an asthma diary database and protocol device 56 that receives asthma-related information from receiving device 54, logs that data in asthma diary database 58, interprets that data according to an asthma treatment protocol 60, and is configured to use display 61 and an uplink to a medical records database to report to the physician and advise the patient of suggested changes in asthma treatment that may help that patient improve her quality of life.

Asthma diary database and protocol device 56 may in some embodiments be combined with receiving device 54 in a combined device 63. Asthma diary database and protocol device 56 typically operates under control of an operating system having communications and display code 62, which may in some embodiments be the operating system of an Android or Apple iPhone cell phone. Asthma diary database and protocol device 56 also operates according to machine readable instructions of diary code 64 that handles recording of asthma symptoms and treatment in asthma diary database 58, and protocol code 66 that uses physician-prescribed protocol 60 to determine treatment recommendations.

In order to at-least-partially automate data gathering, and recording of that data in a patient-specific asthma-diary database, we introduce a wearable sensor 100 (FIG. 2) configured for autonomous detection of asthma symptoms and inhaler use.

This wearable sensor 100 (FIG. 2) is equipped with a digital radio adapted to upload symptom, event, and inhaler-use information to an automated patient-specific asthma-diary database on another machine that may then execute an asthma-management protocol to advise the patient how to better manage asthma, and also provide asthma-diary information to a physician.

Wearable sensor 100 includes a microphone 102, conditioning electronics 104, a processor 106, memory 108, a low power transceiver 110 and a battery 112. Optionally, sensor 100 also includes adhesive 114 for attaching sensor 100 to a user.

In an embodiment, microphone 102 is a ceramic Piezo transducer that is electrically coupled with conditioning electronics 104 that cooperate to convert detected sound into an electrical signal 105. For example, microphone 102 may collect lung and other abdominal sounds when positioned on the torso of a patient. Conditioning electronics 104 includes circuitry that amplifies and/or filters signals from microphone 102 to generate electrical signal 105. Processor 106 executes machine readable instructions of firmware 120, stored within memory 108, to digitize and evaluate electrical signal 105.

Processor 106 may include analog-to-digital conversions circuitry such as found in microcontrollers, known in the art. Upon executing firmware 120, processor 106 analyzes electrical signal 105 to determine whether electrical signal 105 may include sound information relevant to detection of asthma events (e.g., coughing sounds, wheezing sounds, and sounds typical of an inhaler use). If processor 106 determines that signal 105 may include asthma events, processor 106 stores digitized portions of signal 105 as relevant signal 124 within a data buffer 122 of memory 108. Firmware 120 thereby operates to make an initial evaluation of electronic signal 105.

Processor 106, executing instructions of firmware 120, also operates to transmit relevant signal 124 to a receiving device 150 using low power digital transceiver 110. Low power transceiver 110 may implement a low power signal protocol such as Bluetooth Low Energy, Zigbee, or other such protocols, including other body-area network (BAN) protocols, to allow communication between sensor 100 and receiving device 150.

In one embodiment, sensor 100 is in substantially continuous communication with receiving device 150 and communicates substantially all of signal 105 in digitized form to receiving device 150 in real time. In an alternate embodiment, memory 108 is sufficiently large to buffer digitized signal 105 for a certain period, such as when sensor 100 is not communicating with receiving device 150, for example.

Receiving device 150 includes a low power transceiver 152, a processor 154, a memory with firmware 156, and optionally a battery 159 and a communication transceiver 190. In one embodiment, receiving device 150 is selected from the group including: a smart phone, a tablet computer, a personal computer, and so on. Memory 156 stores a signal processing and communications firmware 160 that includes machine readable instructions that when executed by processor 154 operate to receive relevant signal 124 from wearable sensor 100 via low power transceiver 152 and to store relevant signal 124 within a data buffer 158 of memory 156. In one embodiment, signal processing and communications firmware 160 is implemented within an app loaded onto a smartphone used to implement receiving device 150.

Processor 154, executing instructions of signal processing and communications firmware 160, uses a model 162 within memory 156 to identify one or more events 182 within relevant signal 124. In one embodiment, model 162 is pre-trained to recognize events 182. Identified events 182 are stored within an event buffer 180. Event 182 may represent one of a detected cough, a detected wheeze, and detected use of an inhaler. Signal processing and communications firmware 160 and model 162 cooperate to form user-adapting detection through re-adjustment based on previously detected events 182.

Optionally, sensor 100 may include one or more additional sensors 130. Additional sensors 130 may include one or both of: (a) force and/or pressure sensors that assist in better detecting symptom events, and (b) accelerometers that may be used to "clean up" signals that have been corrupted by motion artifact through methods and techniques such as adaptive filtering. In one embodiment, additional sensor 130 is an accelerometer that provides movement information to processor 106, wherein firmware 120 operates to make detected sounds more robust to motion artifacts. For example, a cough typically involves a sharp movement of the chest wall, which may be detected by the accelerometer and used by firmware 120 to qualify detected sounds as coughs. Firmware 120 may also include an adaptive filter process that automatically adjusts filtering of detected sounds.

In an embodiment, signal processing and communications firmware 160 utilizes a layered/multi-level detection approach to make detection of events 182 from relevant signals 124 more robust. For example, signal processing and communications firmware 160 may include a coarse detection first step for detecting sounds that may be coughs from the variety of normal sounds. Then, signal processing and communications firmware 160 utilizes a fine detection step for distinguishing between coughs and very similar sounds such as sneezing and throat clearing. Signal processing and communications firmware 160 may then utilize model 162 to qualify detected events 182. For example, firmware 160 and model 162 may utilize one or more of signal power estimation, pattern recognition, and so on. In one embodiment, firmware 160 and model 162 first extract special features relating to the temporal (e.g., RMS energy), spectral (e.g., MFCCs), statistical (e.g., Mean & std. deviation) characteristics of the relevant signals 124. Firmware 160 then utilizes one or more signal processing (such as template matching), statistical inferencing (e.g., Bayesian methods) and/or pattern recognition/machine learning techniques (e.g., SVM, HMM, DNN classifiers), to qualify and generate events 182. Firmware 160 may, or may not, use statistical/classifier models previously trained over a database of acoustic events. Firmware 160 thereby processes extracted features from relevant signal 124 and generates events 182 with a probability, likelihood, and/or confidence that the event is a particular symptom.

Sensor 100 and signal processing and communications firmware 160 cooperate to form system 101 that aids asthma patients to better manage their symptoms by keeping track of symptom occurrence and medication use.

Sensor 100 and signal processing and communications firmware 160 do not require special upgrades to inhalers to facilitate detection of their use, but rather utilizes electronic auscultation to detect whether inhalation of medication has actually occurred. Sensor 100 also detects sounds from inhaler actuations that are then distinguished and correlated with sounds from auscultation by signal processing and communications firmware 160, using model 162 for example.

In a similar manner, occurrence of cough and wheeze are also detected by sensor 100 and identified by signal processing and communications firmware 160 in correlation with internal sounds of the body. Signal processing and communications firmware 160 processes signals collected from microphone 102, to detect symptom (e.g., coughing, wheezing) and medication events (e.g., use of inhaler) and record them as events 182.

System 101 is configured to operate continuously and autonomously to detect coughs, wheezes and inhaler use when attached to a user. System 101, and in particular sensor 100, has low-power requirements and is unobtrusive since sensor 100 is small and operates autonomously, without human interaction, to record detected events 182. Thus, once sensor 100 is attached to user's (patient's) body, the user may go about their day to day activities without bothering themselves with manually logging their cough, wheeze, and inhaler use. In one embodiment, sensor 100 is similar in form to a Band-Aid®, and is thereby easily applied and comfortable to use. Similarly, where receiving device 150 is implemented as a smart phone often carried by the user, system 101 has minimal impact on the user's actions, and is thereby convenient and unobtrusive. System 101 operates to keep track of asthma symptoms and inhaler use without any effort from the user. Further, since modification to the inhaler is not required for detection of use by system 101, the user may continue to use their current medication and are not required to purchase/obtain other inhalers.

Signal processing and communications firmware 160 and firmware 120 may be configured to operate with a specific user, and may also learn during operation to adapt to the specific user. For example, one or both of firmware 120 and signal processing and communications firmware 160 may include reinforcement learning software that tailors the detection of coughs, wheezes, and inhaler use to the specific user, such that with time, system 101 learns more about the particular user and thereby automatically improves detection of their specific symptoms and inhaler use as compared to a system that does not learn. Thus, system 101 becomes more personalized the more it is used.

Sensor 100 may also include mechanical damping techniques to eliminate motion artifacts caused by one or more of the user's sudden and/or rapid movements and direct disturbances to sensor 100, such as by touching or rubbing, may be eliminated from signal 105 using additional sensors 130 and/or mechanical damping.

Figure 2:
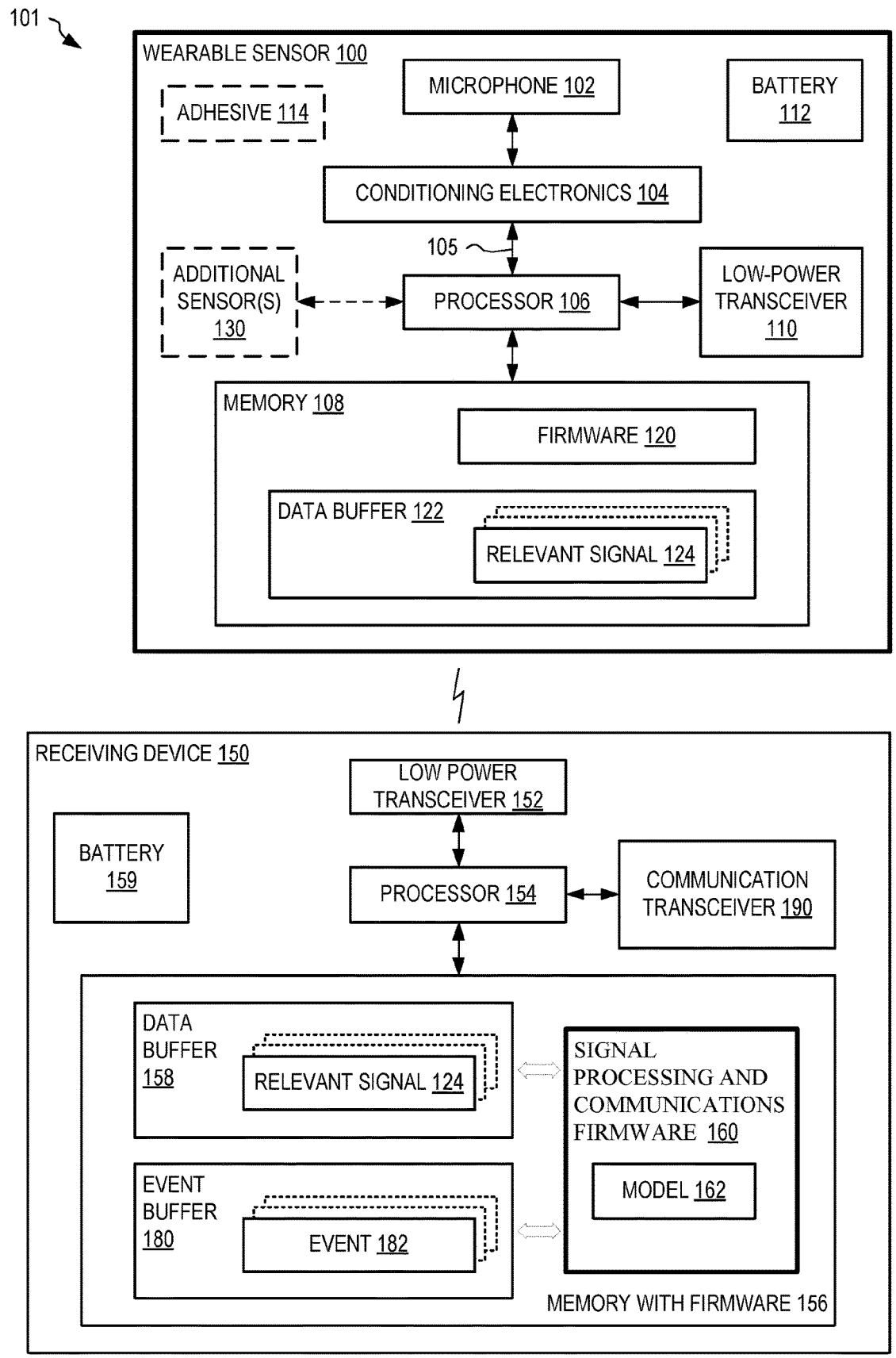
FIG. 2 shows one exemplary wearable sensor for autonomous detection of asthma symptoms and inhaler use, in an embodiment.
Figure 3:
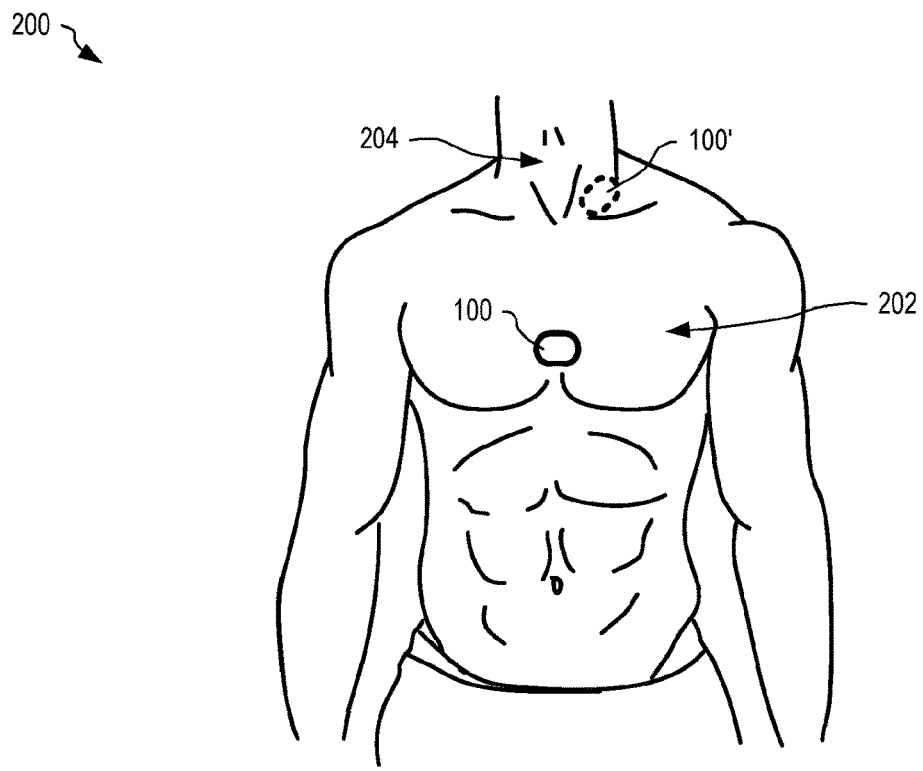
FIGS. 3 and 4 show exemplary positioning of the sensor of FIG. 2 on the user's chest, the user's throat, and the user's back, in embodiments.
Figure 4:
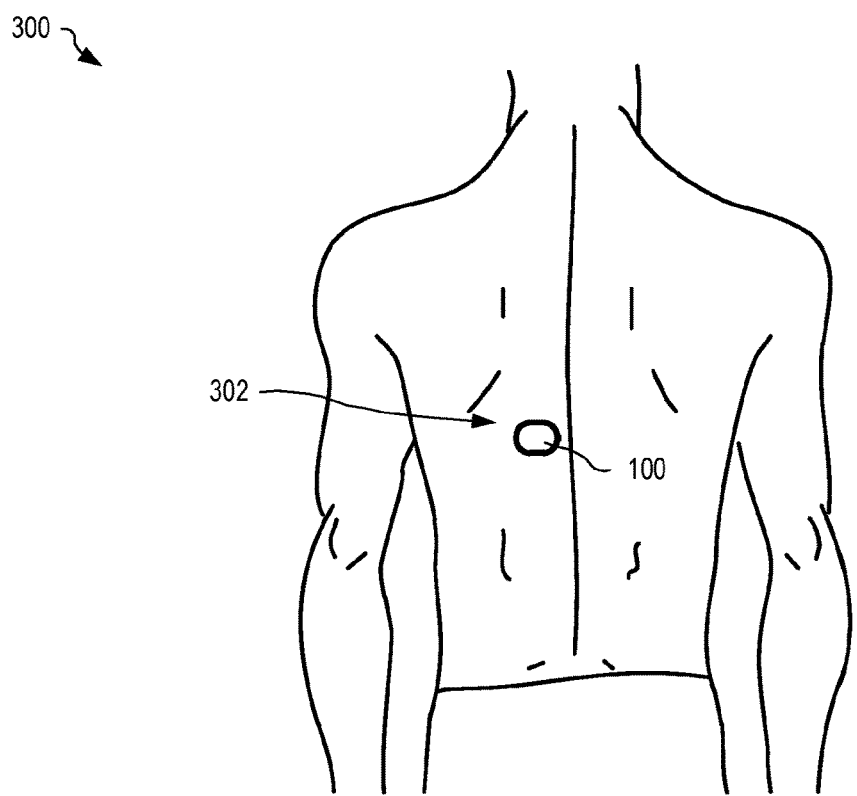

FIGS. 3 and 4 show exemplary positioning of sensor 100 of FIG. 2 on the user's chest 202, the user's throat 204, and the user's back 302.

Figure 5:
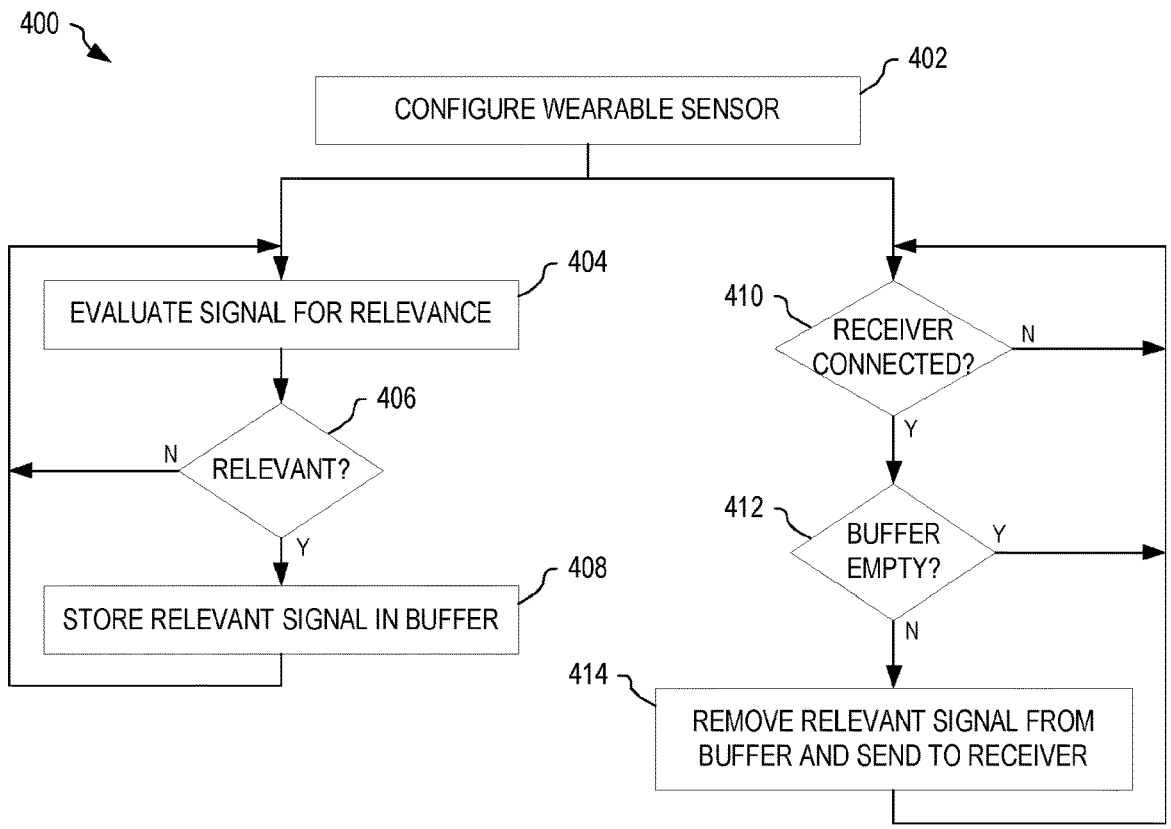
FIG. 5 is a flowchart illustrating one exemplary method for autonomous detection of asthma symptoms and inhaler use, in an embodiment.

FIG. 5 is a flowchart illustrating one exemplary method 400 for autonomous detection of asthma symptoms and inhaler use. Method 400 is for example implemented within firmware 120 of FIG. 2. In step 402, method 400 configures the wearable sensor. In one example of step 402, firmware 120 configures one or more of conditioning electronics 104, processor 106, memory 108, and low-power transceiver 110 for operation. In step 404, method 400 evaluates the signal from the microphone for relevance. In one example of step 404, firmware 120 evaluates signal 105 and determines whether it is relevant to detecting events 182. In another example of step 404, firmware 120 utilizes input from additional sensors 130 to qualify whether signal 105 is representative of events 182.

Step 406 is a decision. If, in step 406, method 400 determines that the signal is relevant, method 400 continues with step 408; otherwise, method 400 continues with step 404.

In step 408, method 400 stores the relevant portion of the signal in a buffer. In one example of step 408, firmware 120 stores relevant signal 124 within data buffer 122 of memory 108.

Steps 404 through 408 repeat to collect and store relevant signal 124 within data buffer 122 when they are determined relevant to detection of events 182.

Step 410 is a decision. If, in step 410, method 400 determines that a receiver is connected, method 400 continues with step 412; otherwise method 400 continues with step 410.

Step 412 is a decision. If, in step 412, method 400 determines that the data buffer is empty, method 400 continues with step 410; otherwise method 400 continues with step 414. In step 414, method 400 removes one relevant signal from the buffer and sends the relevant signal to the receiver. In one example of step 414, firmware 120 removes relevant signal 124 from data buffer 122 and sends the relevant signal 124 to receiving device 150 via low-power transceiver 110.

Steps 410 through 414 repeat, concurrently with steps 404 through 408, to send relevant signals 124 to receiving device 150.

Figure 6:
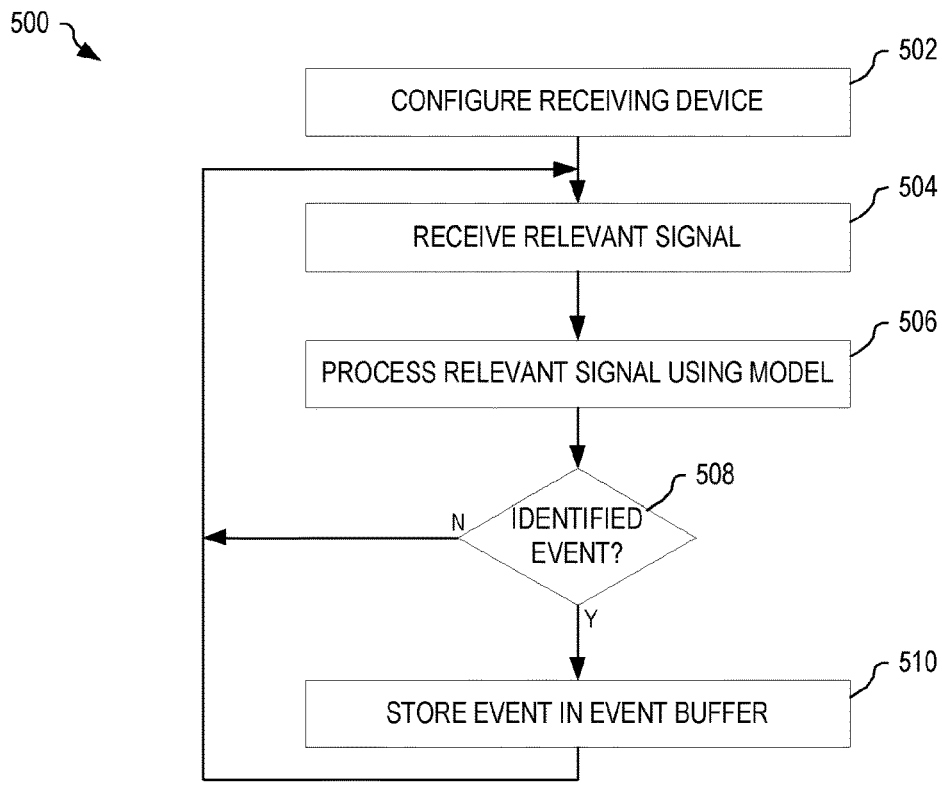
FIG. 6 is a flowchart illustrating one exemplary method for autonomous detection of asthma symptoms and inhaler use, in an embodiment.

FIG. 6 is a flowchart illustrating one exemplary method 500 for autonomous detection of asthma symptoms and inhaler use. Method 500 is for example implemented within signal processing and communications firmware 160 of receiving device 150.

In step 502, method 500 configures the receiving device. In one example of step 502, signal processing and communications firmware 160 configures one or more of low-power transceiver 152, processor 154, and memory 156 of receiving device 150. In step 504, method 500 receives a relevant signal. In one example of step 504, transceiver 152 of receiving device 150 receives relevant signal 124 from wearable sensor 100. In step 506, method 500 processes the relevant signal using a model. In one example of step 506, signal processing and communications firmware 160 processes relevant signal 124 within data buffer 158 using model 162.

Step 508 is a decision. If, in step 508, method 500 determines that an event has been identified, method 500 continues with step 510; otherwise, method 500 continues with step 504. In step 510, method 500 stores the identified event in an event buffer. In one example of step 510, signal processing and communications firmware 160 stores event 182 within event buffer 180.

Steps 504 through 510 repeat to process received relevant signals 124 and to identify events 182 therein.

Figure 7:
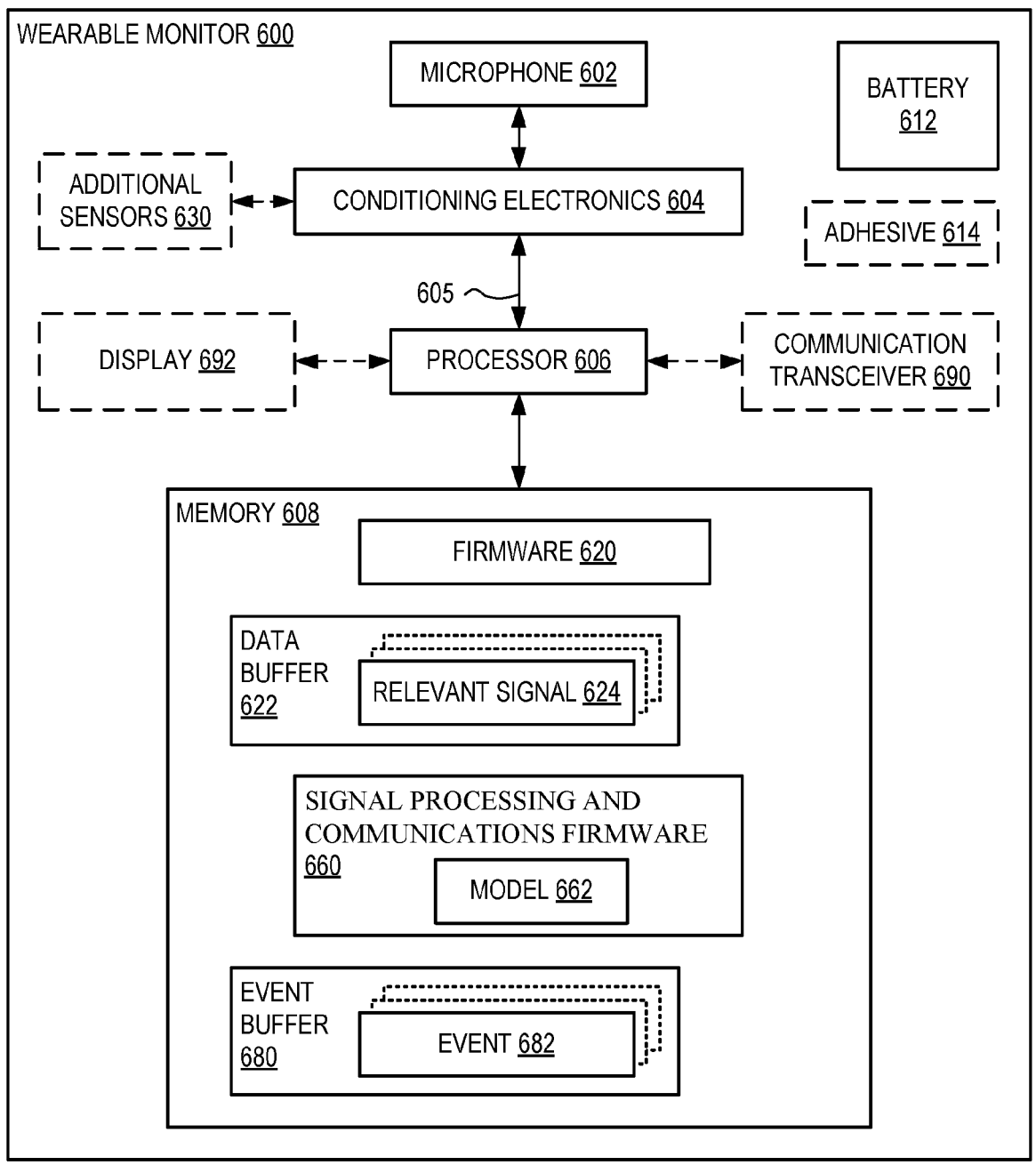
FIG. 7 shows one exemplary wearable monitor for autonomous detection of asthma symptoms and inhaler use, in an embodiment.

FIG. 7 shows one exemplary wearable monitor 600 for autonomous detection of asthma symptoms and inhaler use. Wearable monitor 600 is similar to wearable sensor 100 and receiving device 150 combined. Monitor 600 includes a microphone 602, conditioning electronics 604, a processor 606, memory 608, and a battery 612. Processor 606 executes machine readable instructions of a firmware 620 stored within memory 608 and operates to digitize electrical signal 605. When executing firmware 620, processor 606 analyzes electrical signal 605 to determine whether electrical signal 605 may include sound information relevant to detection of asthma events (e.g., coughing sounds, wheezing sounds, and sounds generated by use of an inhaler). If processor 606 determines that signal 605 may include asthma events, processor 606 stores digitized portions of signal 605 as relevant signal 624 within a data buffer 622 of memory 608.

Further, monitor 600 includes, within memory 608, a signal processing and communications firmware 660 and a model 662. Processor 606, executing instructions of signal processing and communications firmware 660, uses model 662 within memory 608 to identify one or more events 682 within relevant signal 624. In one embodiment, model 662 is pre-trained to recognize events 682. Event 682 may represent one of a detected cough, a detected wheeze, and detected use of an inhaler. Signal processing and communications firmware 660 and model 662 cooperate to form user-adapting detection through re-adjustment based on previously detected events 682.

In an embodiment, to improve life of battery 612, monitor 600 includes two processors (e.g., processor 606 and an additional processor, not shown), such that firmware 620 is executed by a first of the two processors and signal processing and communications firmware 660 is executed by a second of the two processors.

Optionally, monitor 600 includes an adhesive 614 for attaching monitor 600 to the user. In an alternative embodiment, monitor 600 is worn within clothing or is attached using an external mechanism, such as a strap or necklace.

Monitor 600 may also include an optional communication transceiver 690 that allows monitor 600 to transfer events 682 and/or relevant signals 624 to an external device, such as a host computer for recording (e.g., in electronic medical records of the user) and/or further analysis.

Monitor 600 may also include an optional display 692 (e.g., an LCD or LED matric display) that allows monitor 600 to display events 682 and/or relevant signals 624 to a user for recording and/or further analysis.

Optionally, monitor 600 may include one or more additional sensors 630. Additional sensors 630 may include one or both of: (a) force and/or pressure sensors that assist in better detecting symptom events, and (b) accelerometers that may be used to "clean up" signals that have been corrupted by motion artifact through methods and techniques such as adaptive filtering. In one embodiment, additional sensor 630 is an accelerometer that provides movement information to processor 606, wherein firmware 620 operates to make detected sounds more robust to motion artifacts. For example, a cough typically involves a sharp movement of the chest wall, which may be detected by the accelerometer and used by firmware 620 to qualify detected sounds as coughs. Firmware 620 may also include an adaptive filter process that automatically adjusts filtering of detected sounds.

Figure 8:
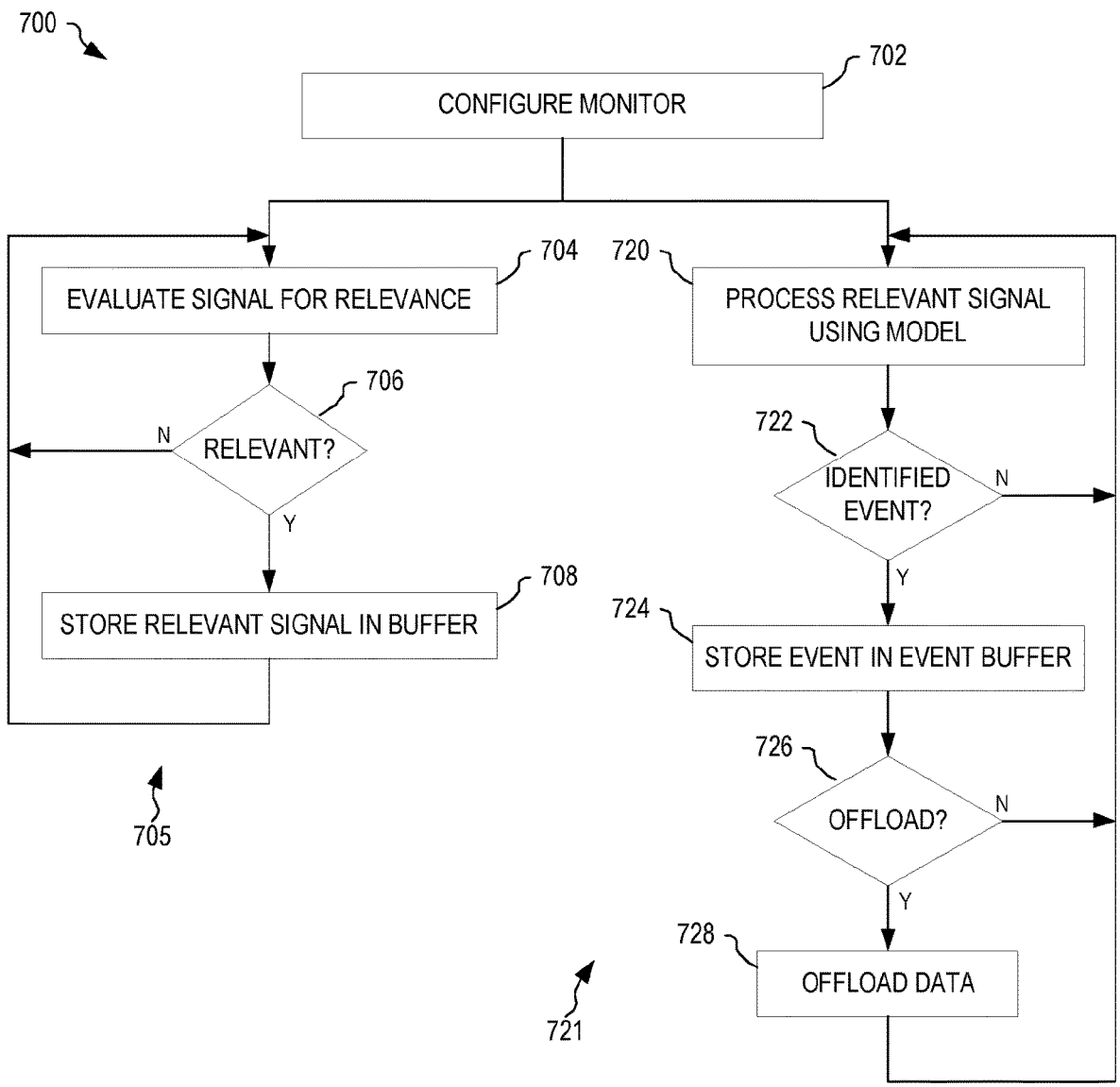
FIG. 8 is a flowchart illustrating one exemplary method, implemented within the wearable monitor of FIG. 7, for autonomous detection of asthma symptoms and inhaler use, in an embodiment.

FIG. 8 is a flowchart illustrating one exemplary method 700 for autonomous detection. Steps 702 through 708 of method 700 are for example implemented within firmware 620 of FIG. 7. Steps 720 through 728 of method 700 are for example implemented within signal processing and communications firmware 660 of FIG. 7.

In step 702, method 700 configures the monitor. In one example of step 702, processor 606 executes machine readable instructions of at least part of firmware 620 and/or machine readable instructions of at least part of signal processing and communications firmware 660 to configure one or more of microphone 602, conditioning electronics 604, processor 606, and memory 608. Optionally, in step 702, processor also configures communication transceiver 690 for communicating with the external device.

Steps 704 through 708 form a loop 705 that repeats to substantially continually process electrical signal 605. Steps 720 through 728 for a loop 721 that repeats to substantially continually process relevant signals 624 identified from electrical signal 605. Loops 705 and 721 may operation substantially in parallel to concurrently process electrical signal 605 and relevant signals 624 identified therein.

In step 704, method 700 evaluates the signal for relevance. In one example of step 704, processor 606 executes machine readable instructions of firmware 620 to evaluate electronic signal 605 to determine its relevance to detecting events 682. Step 706 is a decision. If, in step 706, method 700 determines that a current portion of the electronic signal is relevant, method 700 continues with step 708; otherwise, method 700 continues with step 704. In step 708, method 700 stored the current portion of electronic signal 605 in a buffer. In one example of step 708, processor 606, executing machine readable instruction of firmware 620, stores relevant signal 624 within data buffer 622 of memory 608. Method 700 then continues with step 704.

Steps 704 through 708 repeat to substantially continuously process electronic signal 605, storing digitized portions of electronic signal 065 as relevant signal 624 within data buffer 622 when that portion of the signal may include an event 682. Portions of signal 605 that are not likely to contain events 682 are not stored within buffer 622, thereby reducing the processing by signal processing and communications firmware 620.

In step 720, method 700 processes relevant signal using a model. In one example of step 720, processor 606 executes machine readable instructions of signal processing and communications firmware 660 to evaluate relevant signal 624, if present within data buffer 622, using model 662 to determine whether relevant signal 624 includes an event 682. Step 722 is a decision. If, in step 722, method 700 determines that relevant signal 624 includes an event 682, method 700 continues with step 724; otherwise, method 700 continues with step 720. In step 724, method 700 stores the event in the event buffer. In one example of step 724, processor executes machine readable instructions of signal processing and communications firmware 660 to store event 682 within event buffer 680.

Step 726 is a decision. If, in step 726, method 700 determines that data is to be offloaded, method 700 continues with step 728; otherwise, method 700 continues with step 720. In step 728, method 700 offloads data from the event buffer to an external device. In one example of step 728, processor executes machine readable instructions of signal processing and communications firmware 660 to retrieve one or more events 682 from event buffer 680 and sends these events, via optional communication transceiver 690, to an external computer, such as a doctor's computer. Method 700 then continues with step 720.

Steps 720 through 728 repeat to process each relevant signal 624 within data buffer 622.

Figure 9:
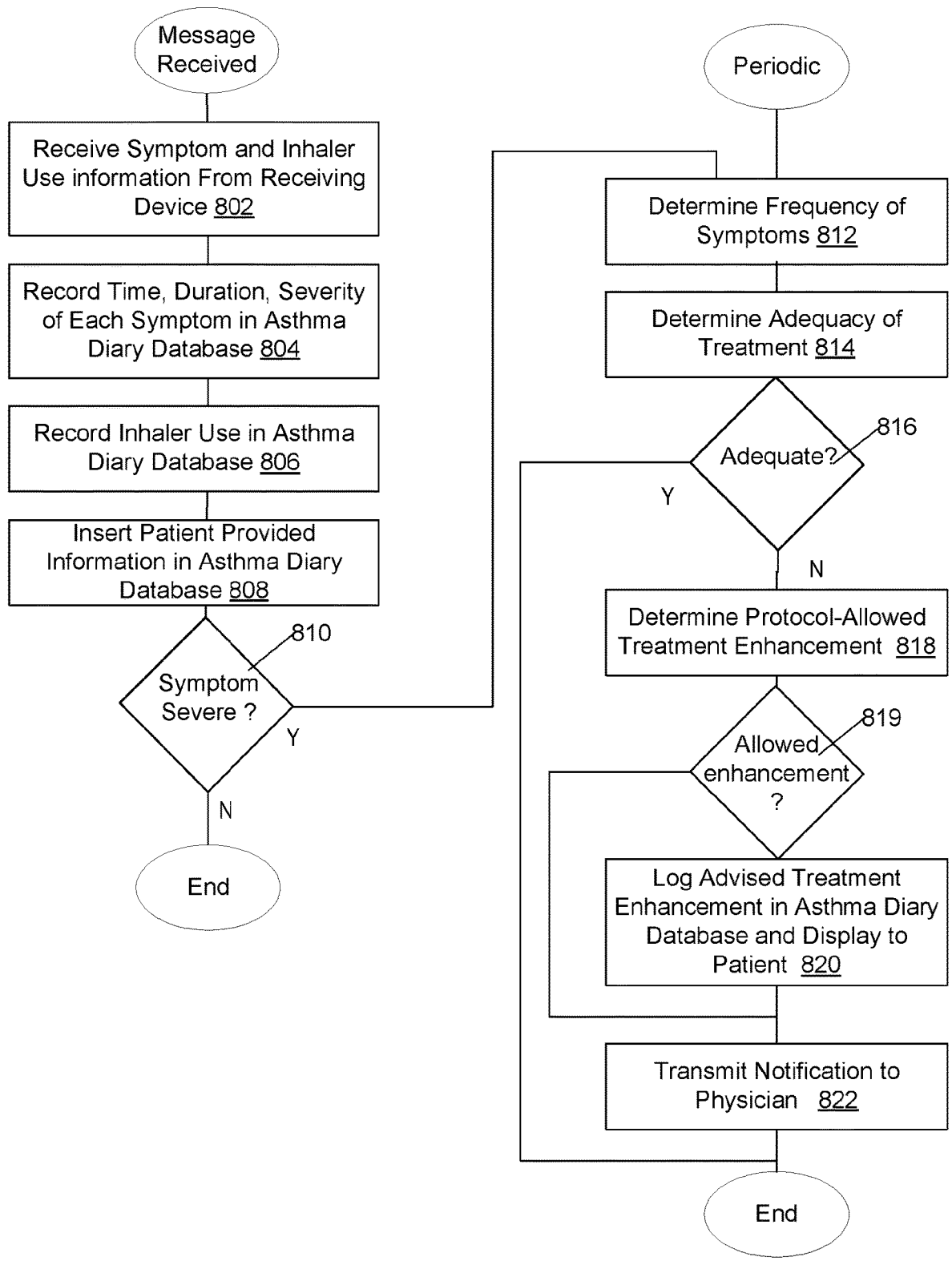
FIG. 9 is a flowchart illustrating some significant portions of the asthma diary and protocol code.

Once events signals are processed, with symptoms such as periods of wheezing, coughing, or decreased expiratory-inspiratory ratio recognized, these symptoms are transmitted to asthma diary and protocol device 56 (FIG. 1), where asthma diary and protocol code (FIG. 9) executes. Similarly, detected inhaler use is transmitted to the asthma diary and protocol device 56 (FIG. 1), where asthma diary and protocol code (FIG. 9) also executes. Symptom events, including severity, duration, and timing, of wheezing and coughing, are received 802 and recorded 804 in asthma diary database 58, as are recorded 806 detected inhaler use with time of use and type of inhaler used. In some embodiments, additional information, such as notes entered by the patient regarding exposures to potential triggers, are also entered 808 into asthma diary database 58. Each time events are entered into asthma diary database 58.

Whenever severe symptoms are detected 810, or periodically, in an one embodiment once daily, symptoms are tallied 812 to determine additional measures traditionally used by physicians to determine adequacy of treatment such as, in an embodiment, frequency of asthma symptoms such as wheezing events, and frequency of "rescue inhaler" (typically beta-agonist inhaler) use. Parameters in protocol 60 (FIG. 1) are applied by protocol code 66 by to recently detected symptom events, the determined frequency of asthma symptoms, and used to determine 816 adequacy of treatment, if treatment is deemed adequate the protocol code ends. If treatment is deemed inadequate, such as when a patient suffers frequent wheezing and requires frequent rescue inhaler use, then protocol code 66 inspects protocol 60 to determine 818 if there is a treatment enhancement, such as a dosage increase of a "controller" medication, frequency of controller inhaler use, or addition of a different type of controller medication, permitted by physician-approved protocol 60. If 819 a protocol-permitted treatment enhancement is found, the patient is advised 820 on display 61 both at the time the treatment enhancement is determined and whenever the patient accesses the asthma diary database and protocol device 56. The treatment enhancement is logged 820 in asthma diary database 58. Whenever treatment is deemed inadequate, a message is sent 822 to the physician and to the patient's electronic health record available to the physician describing symptoms encountered by the patient and any treatment enhancement the patient has been instructed to use.

In a particular embodiment, the protocol 60 is configured to instruct a patient to increase dosage of an inhaled steroid controller medication as a treatment enhancement when symptoms occur frequently, instructions to the patient are provided through a human-readable message comprising those instructions.

It is expected that the asthma diary database 58 will be accessed by the physician whenever the patient visits her physician, the physician will find symptom and treatment data logged in the database of use in managing the patient's asthma. The physician may update prescriptions, provide additional instructions including dosage and medication selection changes to the patient, and modify protocol 60 as appropriate for the patient.

Asthma sometimes has characteristics of obstructive expiration. A patient may retain significantly more air in her lungs at the end of initial expiration during asthma episodes than under normal conditions, this air slowly leaving the lungs between breaths. In some embodiments, an initial inspiration/expiration ratio is computed to quantify this effect, the quantified inspiration/expiration ratio is stored by diary code 64 with detected wheezing and coughing as an asthma symptom in asthma diary database 58 for processing by protocol code 66 and for presentation to treating physicians.

Figure 11:
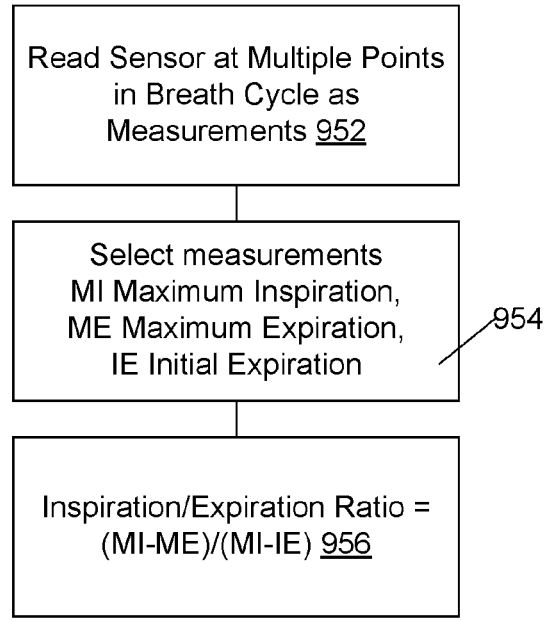
FIG. 11 is a flowchart illustrating detection of inspiratory to initial expiratory volume ratios.

In some embodiments microphone 102 is a piezoelectric device that exhibits a slow signal corresponding to chest-wall breathing motions, this slow signal is superimposed on the audio signal that is processed to detect wheezing and in some embodiments is sufficient to produce a signal representing initial expiration, full expiration, and inspiration. In these embodiments, an inspiration/initial expiration ratio, or an initial expiration/inspiration ratio, is implemented by processing this signal in accordance with FIG. 11 below.

Figure 10:
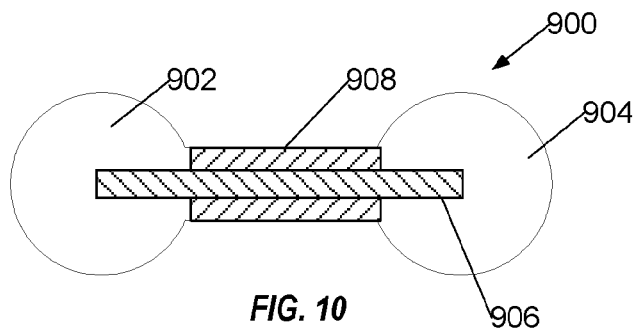
FIG. 10 is a block diagram illustrating an embodiment adapted to detection of inspiratory to initial expiratory volume ratios.

In a particular embodiment implementing an inspiration/initial expiration ratio, or the reverse an initial expiration/inspiration ratio, a housing of wearable sensor 900 (FIG. 10) is flexible having at least two sections 902, 904, that can move relative to each other, or is fabricated with two sections interconnected with a flexible portion, and each section is configured with adhesive for attachment to a subject's chest wall. This version of the sensor is configured for wear over a portion of the chest wall that shifts with a patient's breath cycle such as over the ribcage with each section adhered over a different rib of the ribcage; this embodiment is not intended for placement over a patient's sternum or spine. A mechanical-displacement or strain sensor 908 is provided in this embodiment to quantify displacement between the two sections. In a particular embodiment, a removable plastic handle 906 is coupled to both sections 902, 904 during attachment to a patient to ensure the displacement sensor is within its dynamic range upon attachment; the handle 906 is then removed. Such mechanical-displacement or strain sensors 908 may be fabricated of piezoelectric or piezoresistive materials, may be an optically-encoded displacement sensor, or may be any other displacement or strain sensor that is sufficiently compact to remain unobtrusive on a patient's chest wall.

With this embodiment 900, or with the embodiment where the microphone provides a sufficient breathing chest-wall motion signal, cyclic sensor readings are obtained as the patient's chest wall expands and contracts with breathing. The sensor is read 952 (FIG. 11) at multiple times during the breath cycle to provide measurements. Upon completion of the breath cycle, the measurements are selected 954 to determine a measurement at maximum chest expansion or inspiration, and a measurement at minimum chest size or maximum expiration; sufficient measurements are obtained between the maximum inspiration time and the maximum expiration time to determine a "knee" in in the curve, where chest contraction slows as initial expiration is completed, an initial expiration measurement is obtained at this knee. The inspiration-expiration ratio is determined 956 as a ratio of the difference between measurements at maximum expiration (ME) and maximum inspiration (MI) to the difference between initial expiration (IE) and maximum inspiration.

Combinations of Features

The features and elements of the system for asthma management herein described may be combined in several ways into a useable system. These ways include:

A wearable sensor designated A for autonomous detection of asthma symptoms and inhaler use includes a microphone adapted to generating an electrical signal indicative of asthma symptoms and of inhaler use, a processor, a memory having firmware, the firmware, when executed by the processor, configured to process a portion of the electrical signal to determine whether the portion of the electrical signal potentially corresponds to one or both of the asthma symptoms and inhaler use, and to store the portion of the electrical signal in the memory when the portion of the electrical signal is determined to potentially correspond to one or both of the asthma symptoms and inhaler use. The memory further has a data buffer adapted to store the portion of the electrical signal until it is communicated to an external device; and a housing for the microphone, the memory and the processor.

A wearable sensor designated AA including the wearable sensor designated A, further including adhesive mechanically coupled with an external surface of the housing and capable of removably attaching the housing to the chest, throat or back of a user.

A wearable sensor designated AB including the wearable sensor designated A or AB, the housing comprising mechanical damping adapted to reduce the effect of movement upon the electrical signals.

A wearable sensor designated AC including the wearable sensor designated A, AA, or AB, further including a display for displaying one or both of the detected asthma symptoms and inhaler use.

A wearable sensor designated AD including the wearable sensor designated A, AA, AB, or AC further including a low-power transceiver for communicating the portion of the electrical signal to an external device.

A wearable sensor designated AE including the wearable sensor designated A, AA, AB, AC, or AD the external device selected from the group including a smart phone, a mobile phone, and a tablet computer.

A wearable sensor designated AF including the wearable sensor designated AE, the external device comprising software having machine readable instructions that when executed by a processor of the external device is capable of analyzing the portion of the electrical signal to identify one or both of the asthma symptoms and the inhaler use.

A wearable sensor designated AG including the wearable sensor designated A, AA, AB, AC, AD, AE, or AF, the asthma symptoms comprising at least one of coughing sounds and wheezing sounds.

A wearable sensor designated AH including the wearable sensor designated A, AA, AB, AC, AD, AE, AF, or AG, further including one or more additional sensors for detecting movement information of the user, wherein the movement information is used to determine whether the portion of the electrical signal potentially corresponds to one or both of the asthma symptoms and inhaler use.

A wearable sensor designated AJ including the wearable sensor designated A, AA, AB, AC, AD, AE, AF, AG or AH, further including one or more additional sensors for detecting movement information of the user, wherein the movement information is used to exclude the portion of the electrical signal when corresponding to the movement information.

A wearable sensor designated AK including the wearable sensor designated A, AA, AB, AC, AD, AE, AF, AG, AH, or AJ further including one or more additional sensors for detecting chest-wall movement information of the user, wherein the chest-wall movement information is used by the sensor to determine an inspiratory to expiratory ratio.

An asthma management system designated B including the wearable sensor designated A, AA, AB, AC, AD, AE, AF, AG, AH, AJ, or AK and further comprising an asthma diary database, a protocol, asthma diary firmware, and protocol firmware, the asthma diary firmware configured to store time, severity, and type of asthma symptoms in the asthma diary database.

An asthma management system designated BA including the asthma management system designated B wherein the protocol firmware is adapted to interrogate the protocol upon detection of asthma symptoms, to determine if a treatment enhancement is warranted and permitted according to the protocol and the type and frequency of asthma symptoms, and to advise the patient of a treatment enhancement.

An asthma management system designated BB including the wearable sensor designated A, AA, AB, AC, AD, AE, AF, AG, AH, or AJ, and further including sensors adapted to detect chest-wall movement information of the user, and comprising firmware to use the chest-wall movement information to determine an inspiratory to expiratory ratio. The system also has an asthma diary database, a protocol, asthma diary firmware, and protocol firmware, the asthma diary firmware configured to store time, severity, expiratory and inspiratory ratio, and type of asthma symptoms in the asthma diary database. In this system, the protocol firmware is adapted to interrogate the protocol upon detection of asthma symptoms, to determine if a treatment enhancement is warranted and permitted according to the protocol and the type and frequency of asthma symptoms, and to advise the patient of a treatment enhancement.

A method designated C for autonomous detection of asthma symptoms and inhaler use, including digitizing an electrical signal from a microphone; evaluating a portion of the digitized signal for relevance to the asthma symptoms and for detecting inhaler use; and storing the portion of the digitized signal if it is determined relevant.

A method designated CA including the method designated C, further including: using at least one additional sensor, detecting movement of the user, the step of evaluating further comprising determining the portion of the digitized signal as not relevant because it corresponds to a movement of the user.

A method designated CB including the method designated C or CA, further including displaying the relevant asthma symptoms and inhaler use.

A method designated CC including the method designated C or CB, further including transmitting the portion of the digitized signal to an external device using a low power transceiver.

A method designated CD including the method designated C, CA, CB, or CC, further including: receiving the portion of the digitized signal within the external device; processing the portion of the relevant signal using a model to identify one or more events corresponding to the asthma symptoms and the inhaler use; and storing the one or more events within an event buffer of the external device.

A method designated CE including the method designated C, CA, CB, CC, or CD, further including: logging the one or more events in an asthma diary with event date and time for each event, the one or more events comprising wheezing episodes and inhaler use events; and processing the asthma diary to determine frequency of wheezing episodes.

A method designated CF including the method designated CE, further including evaluating the events with a protocol to determine whether a change of medication is advisable and permitted, and if advisable and permitted then providing instructions in human-readable form instructing of the change in medication.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A wearable sensor for autonomous detection of asthma symptoms and inhaler use, comprising:
    a microphone adapted to electronic auscultation for generating an electrical signal indicative of sounds generated by asthma symptoms and of inhaler use when positioned on a subject's chest;
    a processor;
    a digital radio adapted to transmit detected events to an external device;
    a memory having machine readable instructions stored therein, the machine readable instructions, when executed by the processor, configured to:
        process the electrical signal to determine whether the electrical signal potentially corresponds to sounds indicative of the asthma symptoms and to generate a detected event upon determining that the electrical signal potentially corresponds to sounds indicative of the asthma symptoms;
        process the electrical signal obtained while the wearable sensor is worn by a user and positioned for electronic auscultation of the user to determine whether the electrical signal potentially corresponds to sounds indicative of inhaler use and to generate a detected event upon determining that the electrical signal potentially corresponds to sounds indicative of the inhaler use; and
        store the electrical signal in the memory when the electrical signal is determined to potentially correspond to one or both of the asthma symptoms and the inhaler use;
    a housing containing the microphone, the memory and the processor, the housing being configured for wear on a chest, throat or back of the user; and
    wherein the wearable sensor is not coupled to an inhaler; and
    the machine readable instructions to process the electrical signal comprise instructions to extract features from the electrical signal and instructions for pattern matching using machine-learning-based classifiers to determine when the electrical signal potentially corresponds to sounds indicative of inhaler use and to determine when the electrical signal potentially corresponds to asthma symptoms.

2. The wearable sensor of claim 1, the asthma symptoms comprising at least one of coughing sounds and wheezing sounds.

3. The wearable sensor of claim 1, further comprising one or more additional sensors for detecting movement information of the user, wherein the movement information is used to determine whether the electrical signal potentially corresponds to the inhaler use.

4. The asthma management system of claim 3 wherein the additional sensors comprise sensors adapted to measure chest wall movements of the user.

5. The wearable sensor of claim 1, further comprising one or more additional sensors for detecting movement information of the user, wherein the movement information is used to exclude the electrical signal corresponding to the movement information.

6. The wearable sensor of claim 1, further comprising adhesive mechanically coupled with an external surface of the housing and capable of removably attaching the housing to the chest, the throat or the back of a user.

7. The wearable sensor of claim 1, the housing comprising mechanical damping adapted to reduce an effect of movement upon the electrical signal.

8. The wearable sensor of claim 1, further comprising a display configured for displaying that the electrical signal has been determined to potentially correspond to one or both of the asthma symptoms and inhaler use.

9. The asthma management system of claim 1 wherein the instructions for pattern matching using machine-learning-based classifiers uses a classifier trained on a database of acoustic events.

10. The wearable sensor of claim 1, further comprising machine readable instructions for using the digital radio for communicating the electrical signal to the external device.

11. A system comprising the wearable sensor of claim 10, and the external device selected from the group consisting of a smart phone, a mobile phone, and a tablet computer.

12. The system of claim 11, the external device comprising software having machine readable instructions that when executed by a processor of the external device is capable of analyzing the electrical signal to identify one or both of the asthma symptoms and the inhaler use.

13. An asthma management system comprising the wearable sensor of claim 10, and further comprising an asthma diary database, a protocol, asthma diary firmware, and protocol firmware, the asthma diary firmware configured to store time, severity, and type of asthma symptoms in the asthma diary database.

14. The asthma management system of claim 13, wherein the protocol firmware is adapted to interrogate the protocol upon detection of asthma symptoms, to determine if a treatment enhancement is warranted and permitted according to the protocol and the type and frequency of asthma symptoms, and to advise the user through a display of a determined treatment enhancement.

15. An asthma management system including the wearable sensor of claim 10, and further comprising:
- a receiving device configured to communicate with the wearable sensor;
- sensors adapted to detect chest-wall movement information of a user,
- firmware adapted to use the chest-wall movement information to determine an inspiratory to expiratory ratio,
- an asthma diary database in a memory of the receiving device,
- a protocol in the memory of the receiving device,
- asthma diary firmware, and
- protocol firmware,
- wherein the asthma diary firmware is configured to store time, severity, expiratory and inspiratory ratio, and type of asthma symptoms in the asthma diary database, and the protocol firmware is adapted to interrogate the protocol upon detection of asthma symptoms, to determine if a treatment enhancement is warranted and permitted according to the protocol and the type and frequency of asthma symptoms, and to use the display to advise the user of a treatment enhancement.

* * * * *